United States Patent [19]

Stewart et al.

[11] Patent Number: 4,772,556
[45] Date of Patent: Sep. 20, 1988

[54] GENETICALLY STABLE ALLOPOLYPLOID SOMATIC FUSION PRODUCT USEFUL IN THE PRODUCTION OF FUEL ALCOHOLS

[75] Inventors: Graham G. Stewart; Ingeborg Russell; Chandrakant J. Panchal, all of London, Canada

[73] Assignee: Labatt Brewing Company, Limited, London, Canada

[21] Appl. No.: 883,421

[22] Filed: Jul. 14, 1986

Related U.S. Application Data

[63] Continuation of Ser. No. 532,158, Sep. 14, 1983, abandoned.

[51] Int. Cl.⁴ .................. C12P 7/06; C12N 15/00; C12N 1/18; C12R 1/85
[52] U.S. Cl. .................. 435/161; 435/172.2; 435/256; 435/940; 935/61; 935/69; 935/97; 935/109
[58] Field of Search .......... 435/171, 172.2, 940, 435/941, 161, 255, 256; 935/37, 61, 69, 97, 109

[56] References Cited

U.S. PATENT DOCUMENTS 4,172,764 10/1979 Heslot et al. ............... 435/172.2

OTHER PUBLICATIONS

Panchal et al., *Biotechnology Letters*, 4(1), pp. 33–38, Jan. 1982.

Stewart et al., Royal Society of Canada's International Symposium on Ethanol from Biomass, Oct. 13–15, 1982.
Stewart et al., Second Conference on Whiskey Production and Related Processes, Sep. 8 and 9, 1981.

*Primary Examiner*—Elizabeth Weimar
*Attorney, Agent, or Firm*—Fisher, Christen & Sabol

[57] ABSTRACT

The present invention relates to a stable, allopolyploid, somatic fusion product useful in the fermentation arts and especially in the production of fuel alcohols. More particularly, the present invention relates to a novel allopolyploid yeast strain, *Saccharomyces diastaticus* NCYC 1460, which is the product of the spheroplast fusion of:

(a) a hybrid, diploid strain of *Sacch. diastaticus*; and
(b) a fusion partner which is a polyploid brewing yeast strain of the species *Saccharomyces uvarum (carlsbergensis)*.

The fusion product of the present invention is capable of an enhanced rate of fermentation and a generally higher degree of final attenuation than is typical of either of the fusion partners. Moreover the fusion product also evidences enhanced osmo- and thermo-tolerances and its multiple, non-allelic DEX gene complement renders the organism well suited to the fermentation of substrates containing dextrins and oligosaccharides.

8 Claims, 5 Drawing Sheets

CHARACTERISTICS OF FUSION PARTNERS AND FUSION PRODUCT

CHARACTERISTICS OF FUSION PARTNERS AND FUSION PRODUCT

Saccharomyces diastaticus

Saccharomyces uvarum
(carlsbergensis)

Fusion Product 2 mm

- PARENT SACCHAROMYCES UVARM(CARLSBERGENSIS) STRAIN
- STRAIN NCYC 1460-FUSION PRODUCT

- PARENT SACCHAROMYCES UVARUM(CARLSBERGENSIS) STRAIN
- STRAIN NCYC 1460- FUSION PRODUCT

GENETICALLY STABLE ALLOPOLYPLOID SOMATIC FUSION PRODUCT USEFUL IN THE PRODUCTION OF FUEL ALCOHOLS

This application is a continuation, of application Ser. No. 532,158, filed Sept. 14, 1983.

FIELD OF THE INVENTION

The present invention relates to a genetically stable, allopolyploid, somatic fusion product useful in the fermentation arts, and more particularly, to a novel allopolyploid strain of the species *Saccharomyces diastaticus*.

BACKGROUND OF THE INVENTION

It has been a long standing objective in the fermentation arts to isolate and identify or to otherwise secure species and strains of yeast that are particularly adapted and well suited to the fermentation processes used in the production of alcohols. Yeasts particuarly suited to such applications must ferment the substrate medium in a reasonable period of time to produce between four and twelve per cent weight by volume of ethanol. The yeast should be readily cropped at the end of the fermentation and the collected cell mass should be sufficiently viable that it can be utilized to pitch subsequent fermentations with a high degree of confidence. Perhaps most important to a commercial scale operation where the repeated and constant quality of the yeast's performance is paramount, however, is the genetic stability of the yeast strain. Such strains must lend themselves to repeated use over long periods of time without incurring any substantial genetic changes. One attempt at producing an amalgam of the strong attenuating characteristics of a wild type, non-brewing, yeast strain with the otherwise desirable fermentation characteristics of an established brewery yeast is described in U.K. Patent Specification 1,212,437. In that patent, Windisch et al describe the production of Z16 diploid hybrids which are produced from classical hybridization techniques in a hybrid cross between a haploid B12/14 strain of *Saccharomyces uvarum (carlsbergensis)* brewers' yeast and a wild type Z1-2C strain having the ability to attenuate dextrins. While the recrossing of the resulting Z16 hybrids allows a good deal of versatility in addressing the various problems encountered in differing fermentation systems, the hybrid strain only has a diploid genome. In this latter respect, the Z16 hybrids do not lend themselves well to commercial scale applications.

It will be appreciated that $a/\alpha$ mating type diploids are in effect "neuter" strains with little or no propensity towards sexual activity and, from that point of view, may be considered to be genetically stable. Such mating type diploids, however, are extremely susceptible to environmental stress such as, for example, starvation, and respond to these commonly encountered stresses by producing mixtures of viable a and $\alpha$ mating type haploid spores.

Thus, not only are the carefully engineered advantages of the original diploid hybrid lost, but under more favourable environmental conditions, those spores mate to produce arbitrary recombinations of diploid genotypes. This is particularly detrimental when such mating involves contaminant organisms whose dominant gene characteristics are then incorporated into the resulting diploids, in view of the completely unpredictable results that ensue from such a cross.

$a/a$ and $\alpha/\alpha$ mating type diploid hybrids are even less stable than the $a/\alpha$ types in that the strains which are homozygoris for the mating type allele are additionally prone to diploid sexual recombination.

The Z16 diploid genome therefore is subject to statistical variation that on the balance of probabilities is likely to lead to fundamental changes in both the character and quality of the product produced in the fermentation process over a period of time. In this latter regard, it will be remembered that industrial yeast strains, including brewing and distilling strains, are often polyploid or even aneuploid and, as a consequence, do not possess mating types, have a low degree of sporulation and have a low degree of spore viability, all of which contribute to their overall genetic stability. The widespread use of such polyploid yeasts for industrial purposes, therefore, does not appear to be merely an historical artifact. Furthermore, owing to their multiple gene structure, polyploids are genetically more stable and less susceptible to mutational forces than either haploid or diploid strains. This allows such polyploid yeasts to be used routinely with a much higher degree of confidence in the expectation of their continued and consistent performance than is possible with haploid or diploid strains.

More recently an attempt has been made, see R. S. Tubb et al, EBC Congress 1982, pg. 487, at crossing a poly-diploid brewers' yeast strain of *Sacch. uvarum (carlsbergensis)*, NCYC 1324, with a and $\alpha$ mating type haploid strains of *Sacch. diastaticus*, using rare mating techniques coupled with respiratory markers to indicate successful hybridizations.

One of these latter crosses utilized a *Sacch. diastaticus* haploid strain, BRG 160B which is characterized as being a producer of extracellular glucoamylase. The resulting hybrid, however, showed only a marginally improved fermentative potential over the *Sacch. uvarum (carlsbergensis)* strain.

In another cross, yet another *Sacch. diastaticus* haploid strain was used, BRG 514A which is a known producer of extracellular glucoamalyse. The resulting hybrid was also found to produce ferulic acid decarboxylase, an enzyme which decarboxylates ferulate to produce 4-vinylguaiacol which in turn contributes a phenolic off-flavour to beverages containing that substance. This latter hybrid was then induced to sporulate in the hope that reducing the ploidy of the hybrid would eliminate certain characteristics which are considered undesirable in the brewing of potable alcohols. Once the asci were dissected and the few viable spores isolated and germinated, one strain was found to be devoid of these undesirable characteristics and yet continued to be capable of producing extracellular glucoamylase. None of the hybrids produced by Tubb et al, however, were capable of degrading any more than about 25% of the wort dextrins, since the dextrinase enzymes produced by these hybrids were incapable of hydrolysing $\alpha$-1,6 glucosidic linkages.

Attempts have also been made at crossing a polyploid *Sacch. uvarum (carlsbergensis)* brewing strain with a polyploid *Sacch. diastaticus* strain using somatic fusion techniques. Somatic fusion techniques are generally disclosed in U.S. Pat. No. 4,172,764 - Heslot et al. While fusion products could be formed, fermentative ability was poorer than that of the *Sacch. uvarum (carlsbergensis)* parent and both maltose and dextrin fermentation rates were reduced in comparison with those of either of the fusion partners.

It is an object of the present invention to provide a novel allopolyploid yeast strain suitable for the production of fuel alcohols.

SUMMARY OF THE INVENTION

In one aspect of the present invention there is provided an allopolyploid yeast strain, *Sacch. diastaticus* NCYC 1460 which is the product resulting from the somatic fusion of two selected fusion partners.

The first such fusion partner was a respiratory deficient mutant corresponding to a hybrid diploid strain of *Sacch. diastaticus*, which mutant carried a respiratory deficient marker, i.e. it was unable to grow on lactate media. This strain exhibited growth at 37° C., was unable to ferment melibiose, and it was homozygous recessive in respect of maltose-related genes, i.e. it did not possess the specific MAL genes and it was therefore unable to produce maltose permease and/or α-glucosidase. It was constructed to have a multiple, non-allelic, glucoamylase gene complement and was capable of fermenting dextrin material. It elicited small, smooth, colonial morphology, and was a diploid strain, corresponding respiratory sufficient strains of which were capable of producing many tetraspored asci. Spores derived from these asci could be germinated to produce respiratory sufficient haploid cells.

The second fusion partner was a strain of *Sacch. uvarum (carlsbergensis)* which was capable of growth on lactate media and which fermented melibiose. This strain, however, would not grow at temperatures of 37° C. nor was it capable of fermenting dextrins. The strain was shown to possess MAL genes and was found to be a polyploid capable of only rare spore production. Colonies of this strain had large, smooth morphologies.

The resultant fusion product was found to have rate of fermentation and final attenuation characteristics superior to those of either fusion partner. In addition, the fusion product was found to produce ethanol at a faster rate in synthetic media comprising thirty per cent, weight by volume, glucose, than either the above-mentioned *Sacch. diastaticus* fusion partner or a wild type *Sacch. diastaticus* strain having an undefined polyploid genotype. The fusion product was also determined to be an efficient ethanol producer, highly osmotolerant, capable of fermenting glucose at 40° C., and ordinarily very genetically stable.

Therefore, in accordance with a broad aspect of the present invention, there is provided a novel strain of *Sacch. diastaticus*, strain NCYC 1460. More particularly, the present invention relates to biologically pure cultures of *Sacch. diastaticus*, strain NCYC 1460, and even more particularly to the novel genome therein contained and characterized by virtue of its derivation.

Processes in which the present invention are applicable include, for example, those described in the "Encyclopedia of Chemical Technology", Volume 1, pages 225 through 277. Such processes are all fermentation processes, as distinguished from synthetic processes, and are typically classed according to the nature of the materials used to produce the mash or wort: (1) saccharine; (2) starchy; or (3) cellulosic materials. The particulars of such processes, including the steps required in the preparation of the wort, the recovery of the alcohol and yeast, et cetera, are well known and understood in the art and as these do not impinge per se on the present invention, need not be further described herein.

In another aspect of the present invention therefore there is provided a process for the production of fuel alcohols comprising the steps of preparing a fermentable mash; fermenting the mash; and, recovering the fuel alcohol thereby produced; wherein the improvement comprises fermenting said mash with *Sacch. diastaticus* strain NCYC 1460. It is preferred, however, that the mash be derived from one of a starchy or a saccharine material. It is even more preferable, in the case of a saccharine material, that the readily fermentable carbohydrate source comprises a preponderance of glucose. This process is particularly advantageous in the production of fuel alcohols when the glucose is present in a ratio of about thirty per cent weight by volume of the mash. The term "mash" as used herein will be understood to include worts produced from such mashes.

DETAILED DESCRIPTION OF THE PRESENT INVENTION

During the course of this portion of the description reference will be made to the appended drawings in which:

FIG. 1 lists in tabulative form the characteristics of fusion partners and the fusion product of the present invention;

FIG. 2 depicts the fermentation characteristics of two Sacch. species, one being the fusion product of the present invention, in twenty per cent (w/v) glucose peptone-yeast extract medium at a fermentation temperature of about 40° C.;

FIGS. 3a and 3b illustrate the fermentation characteristics at 30° C. of three Sacch. species containing dextrin genes, including the novel fusion product of the present invention, in thirty per cent (w/v) glucose peptone-yeast extract medium; and, FIGS. 4, 5 and 6 illustrate the respective giant colony morphologies of the diploid *Sacch. diastaticus* parent, the *Sacch. uvarum (carlsbergensis)* parent, and the fusion product of the present invention, *Sacch. diastaticus* strain NCYC 1460.

Figure 9A:
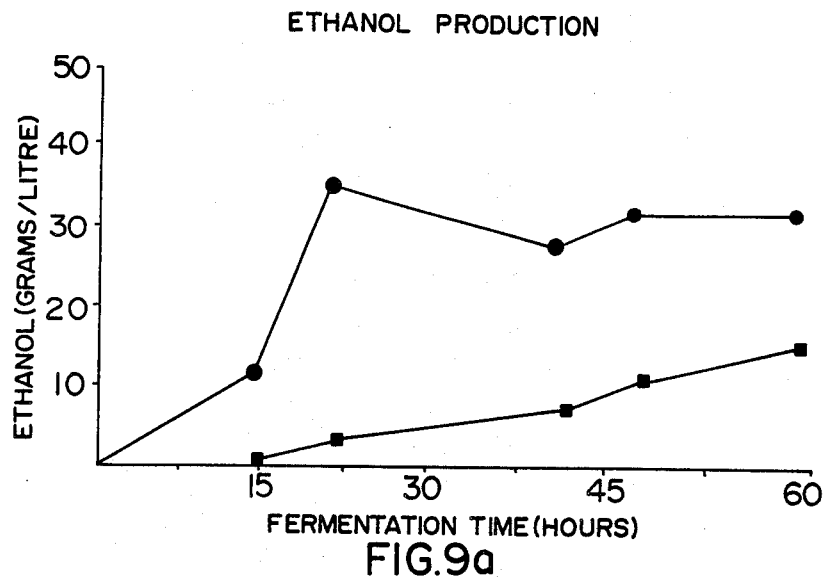
Figure 9B:
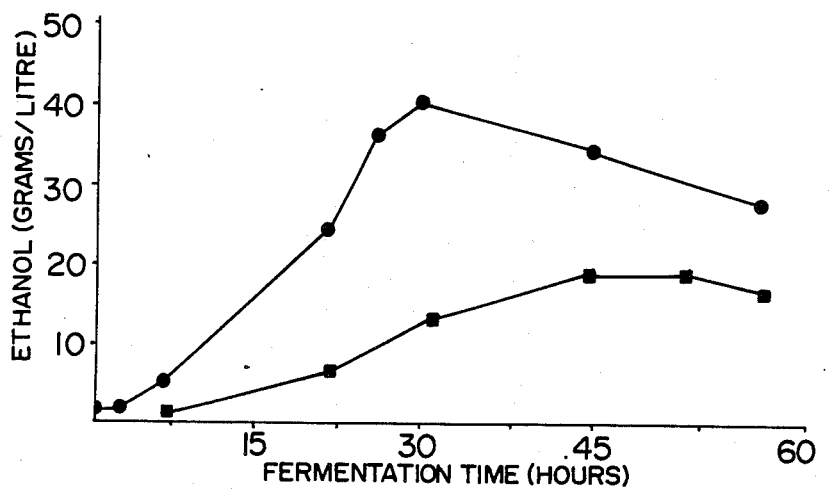

FIGS. 9a and 9b illustrate osmotolerance in media containing 100 g/l of glucose as a carbohydrate and 300 g/l of nonfermentable D-mannitol (FIG. 9a) and D-sorbitol (FIG. 9b) of the parent brewing strain and the fusion product of the present invention.

Figure 1:
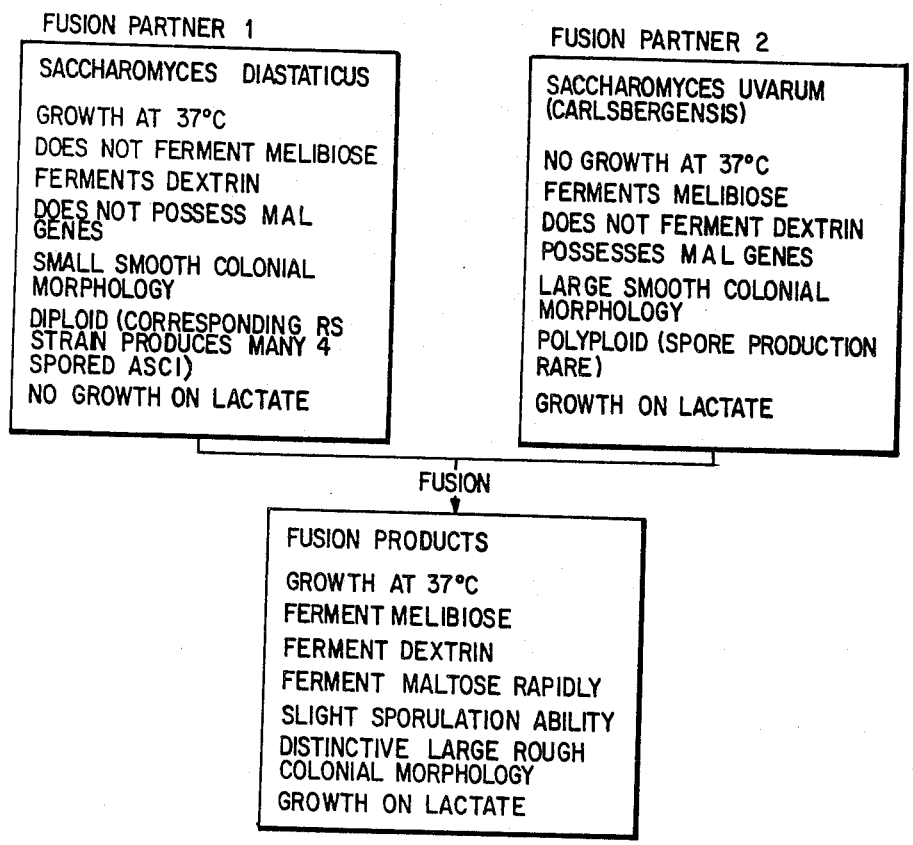

Referring now to FIG. 1 of the drawings, there is shown a schematic summary of the respective characteristics of each of the fusion partners and also of the fusion product. It is important to note that a respiratory sufficient counterpart of the first fusion partner, the parent strain of *Sacch. diastaticus*, was a hybrid diploid strain capable of producing many tetraspored asci, the haploid spores of which were demonstrably respiratory sufficient. Also, the second fusion partner, the polyploid strain of *Sacch. uvarum (carlsbergensis)* produced very few viable spores. In contrast, the fusion product which by virtue of its other characteristics can be shown to be an allopolyploid strain possessing genotypic characteristics derived from both of the respective fusion partners, showed an intermediate ability to produce spores. This suggests that the allopolyploid fusion product underwent some form of spontaneous reduction in ploidy following fusion which resulted in a lower, but more stable, allopolyploid state. Notwithstanding that reduction, however, certain advantageous combination of characteristics derived from the respective fusion partners were retained in the stabilized allopolyploid genotype of *Sacch. diastaticus*, strain NCYC 1460.

Accordingly, the novel allopolyploid yeast strain is characterized in part, by its ability to grow at 37° C. which, of course, distinguishes it from the *Sacch. uvarum (carlsbergensis)* fusion partner which at best produces only nominal growth at the same temperature. Quite surprisingly, the fusion product has also been found to be more thermo-tolerant than even the *Sacch. diastaticus* parent, at least to the extent that thermal tolerance can be measured by virtue of the respective yeast strains' performances in glucose up-take and ethanol production at elevated temperatures.

Figure 2:
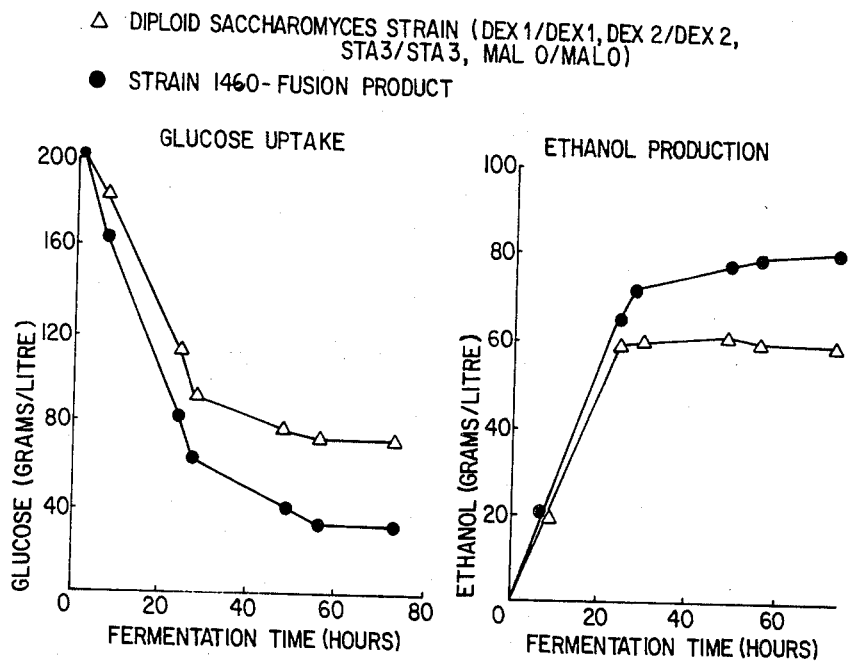

FIG. 2 illustrates these two strains' respective performances in regard to these two parameters on twenty per cent weight by volume glucose-peptone yeast extract medium, at a fermentation temperature of 40° C. The ability of the fusion product to ferment glucose at relatively elevated temperatures is of considerable industrial significance in that the fermentation need not be temperature controlled to the same extent as might be required for fermentations using, for example, strains of *Sacch. uvarum (carlsbergensis)*.

The fusion product also possesses the combined ability to ferment melibiose, raffinose, a large proportion of the dextrins present in a starchy mash and to rapidly ferment maltose. By virtue of the combined presence of the MAL genes and the dextrin genes, the fusion product of the present invention shows an enhanced rate of fermentation of lower molecular weight saccharides. Surprisingly, the novel fusion product also shows an enhanced rate of glucose fermentation.

The fusion product strain significantly out-performs its parent strains on media providing a readily fermentable source of carbohydrate such as glucose in respect of both the up-take of the glucose and in ethanol production.

Figures 3A, 3B:
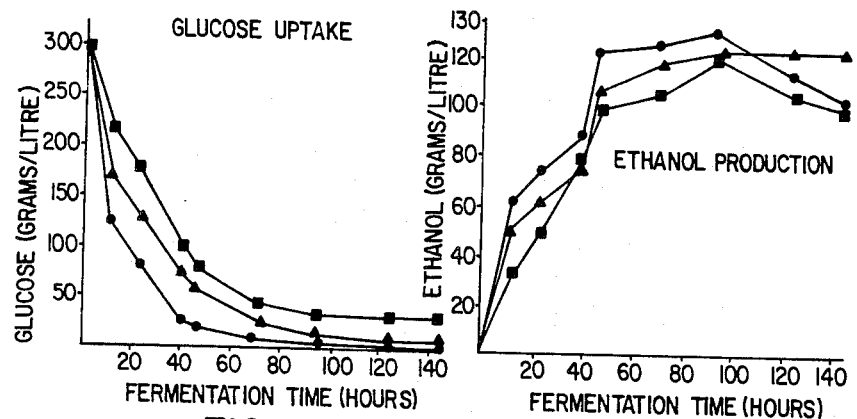

FIGS. 3a and 3b illustrate the relative performance of each of the respective strains in thirty per cent weight by volume glucose-peptone yeast extract medium.

More specifically, FIG. 3a depicts the relative rates of glucose uptake from the above-mentioned nutrient medium. It is important to note that not only is the rate of glucose uptake by the fusion product faster than either of the other two *Sacch. diastaticus* strains represented on the graph, but furthermore, the absolute degree of attenuation of the glucose present in the nutrient medium is significantly greater in the case of the fusion product in comparison with the other above-mentioned strains. Of at least equal significance is the rate at which these respective strains produce ethanol. FIG. 3b is a graphic representation of the relative rates of ethanol production over time in the same thirty per cent weight by volume glucose-peptone-yeast extract medium.

In the course of evaluating these rates of ethanol production, it was noted that the fusion product, strain NCYC 1460, produced 12.2% weight by volume ethanol in forty-eight hours, whereas its diploid parent produced 10.5% weight by volume and another *Sacch. diastaticus* strain, a genetically undefined wild type, produced only 9.8% weight by volume ethanol in the same time period.

Figure 4:
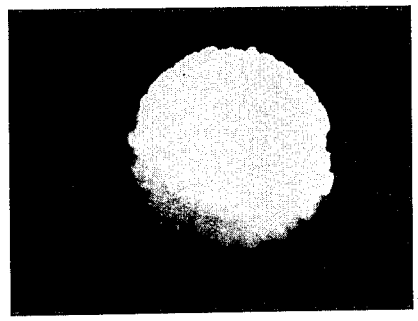
Figure 5:
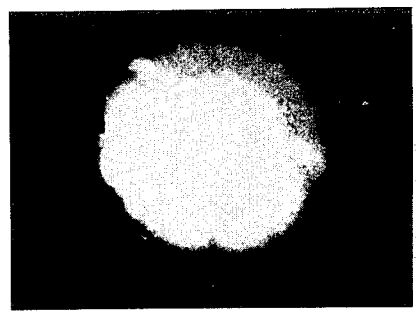
Figure 6:
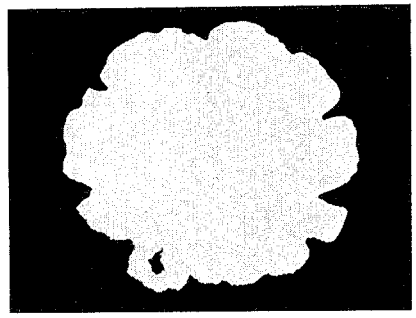

FIGS. 4, 5 and 6 depict the respective giant colony morphologies of the diploid *Sacch. diastaticus* parent, the *Sacch. uvarum (carlsbergensis)* parent and the fusion product, strain NCYC 1460. The pronounced differences in the respective morphologies of these organisms further illustrate the fact that strain NCYC 1460 is a genetically distinct spheroplast fusion product resulting from the fusion of the two parent strains and that strain NCYC 1460 is genetically distinct therefrom. The illustrated colonies were propagated in a manner and on a medium similar to that disclosed by M. Richards in the Journal of the Institute of Brewing, Volume 73, 1967.

Figure 7:
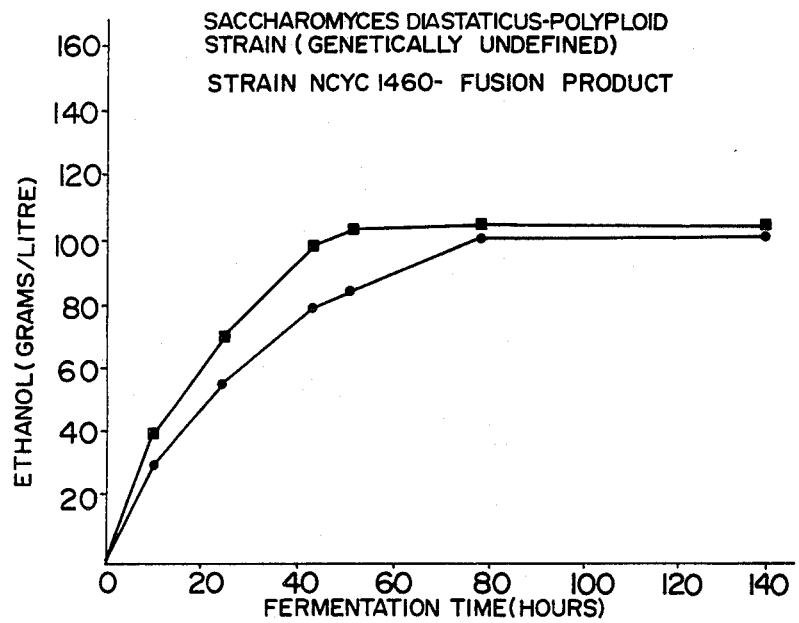
FIG. 7 depicts a graphic comparison of the respective performances of a wild type, polyploid/aneuploid strain of *Sacch. diastaticus* and the fusion product of the present invention, in the production of ethanol from a whole corn mash of 24.8° Plato.
Figure 8:
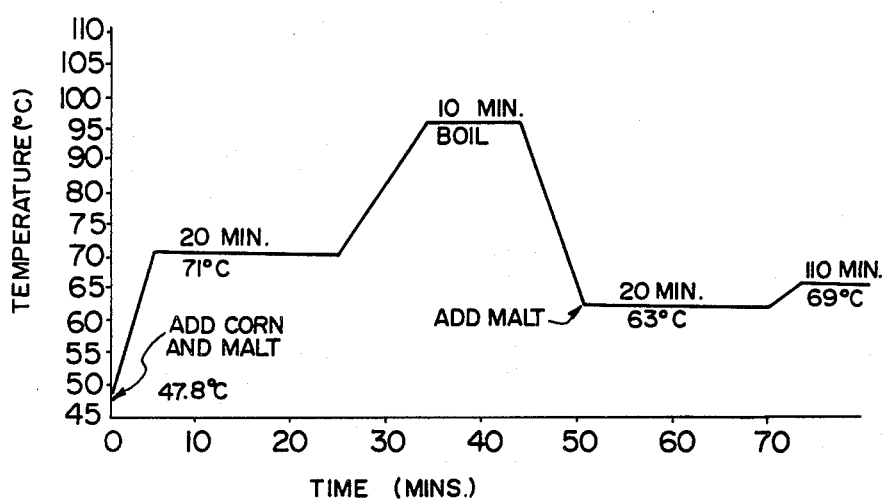
FIG. 8 depicts the mash cycle utilized in the production of the above-mentioned whole corn mash.

Referring now to FIG. 7 the respective ethanol concentrations over time of a strongly fermentative polyploid/aneuploid wild type strain of *Sacch. diastaticus* and the fusion product of the present invention illustrate the strongly fermentative characteristics of the fusion product on whole corn mashes containing high concentrations of dextrins and oligosaccharides. The whole corn mash was prepared in accordance with the mash cycle illustrated in FIG. 8. Moreover the fusion product, unlike the highly flocculating wild type strain does not give rise to flocculation related problems in inoculum preparation. The fermentation from which this data was derived was carried out in a shake flask at 30° C.

Referring now to FIGS. 9a and 9b the osmotolerance of the fusion product is compared with that of its parent brewing strain in terms of the effect of, respectively, D-mannitol and D-sorbitol induced osmotic pressures (concentrations of 300 gms/l were used) on ethanol production from media containing 100 g glucose/l, over time. The high osmotolerance of the fusion products NCYC 1460 is a highly desirable attribute in industrial yeast utilized in fuel alcohol production where efficient fermentation must often be carried out in high gravity substrates.

We claim:

1. A novel strain of *Saccharomyces diastaticus*, strain NCYC 1460.

2. A biologically pure culture of *Saccharomyces diastaticus*, strain NCYC 1460.

3. A novel genome comprising a multiple non-allelic dextrin gene complement and consisting essentially of the genome present in cells of *Saccharomyces diastaticus*, strain NCYC 1460.

4. A process for the production of fuel alcohols comprising the steps of preparing a fermentable mash; fermenting the mash; and, recovering the fuel alcohol thereby produced; wherein the improvement comprises fermenting said mash with *Saccharomyces diastaticus*, strain NCYC 1460.

5. The process of claim 4 wherein said fermentable mash is a whole corn mash.

6. The process of claim 5 wherein said whole corn mash is prepared by adding corn and malt to the mash water at a temperature of about 48° C.; raising the temperature of the resulting mixture to about 71° C. and holding the mixture at that temperature for about 20 minutes; thereafter raising the temperature further to bring the mixture to a boil for about 10 minutes; then reducing the temperature of the mixture to about 63° C., adding additional malt to the mixture, and holding the thus augmented mixture at this temperature for about 20 minutes; then raising the temperature of the mixture to about 68° C. for about 2 hours to complete the mashing process.

7. The process of claim 4 wherein said mash comprises thirty percent glucose by weight of the mash.

8. The process of claim 6 wherein the proportions of malt and corn are selected to yield a final mash of about 25° P.

* * * * *